US012642434B2

(12) United States Patent (10) Patent No.: US 12,642,434 B2
Lee et al. (45) Date of Patent: Jun. 2, 2026

(54) CALIBRATION CRADLE FOR THREE-DIMENSIONAL SCANNER

(71) Applicant: MEDIT CORP., Seoul (KR)

(72) Inventors: Dong Hoon Lee, Seoul (KR); Young Seok Jeong, Seoul (KR)

(73) Assignee: MEDIT CORP., Seoul (KR)

( * ) Notice: Subject to any disclaimer, the term of this patent is extended or adjusted under 35 U.S.C. 154(b) by 354 days.

(21) Appl. No.: 18/276,989

(22) PCT Filed: Feb. 15, 2022

(86) PCT No.: PCT/KR2022/002202
§ 371 (c)(1),
(2) Date: Aug. 11, 2023

(87) PCT Pub. No.: WO2022/177259
PCT Pub. Date: Aug. 25, 2022

(65) Prior Publication Data
US 2024/0115138 A1 Apr. 11, 2024

(30) Foreign Application Priority Data

Feb. 16, 2021 (KR) ........................ 10-2021-0020463

(51) Int. Cl.
*A61B 5/00* (2006.01)
*A61B 1/00* (2006.01)
(Continued)

(52) U.S. Cl.
CPC ........ *A61B 5/0068* (2013.01); *A61B 1/00057* (2013.01); *A61B 1/24* (2013.01);
(Continued)

(58) Field of Classification Search
CPC ............... A61B 5/0068; A61B 5/0088; A61B 2560/0223; A61B 2560/0456; A61B 1/24
See application file for complete search history.

(56) References Cited

U.S. PATENT DOCUMENTS

| | | | |
|---|---|---|---|
| 2003/0011703 A1* | 1/2003 | Tanaka | H04N 21/433 |
| | | | 348/207.1 |
| 2003/0068079 A1 | 4/2003 | Park | |

(Continued)

FOREIGN PATENT DOCUMENTS

| | | |
|---|---|---|
| CN | 105378426 A | 3/2016 |
| CN | 109525799 A | 3/2019 |

(Continued)

OTHER PUBLICATIONS

International Search Report for PCT/KR2022/002202 dated May 23, 2022 [PCT/ISA/210].

(Continued)

*Primary Examiner* — Joel F Brutus
(74) *Attorney, Agent, or Firm* — Sughrue Mion, PLLC

(57) ABSTRACT

The present disclosure relates to a calibration cradle for a three-dimensional scanner. In particular, the calibration cradle includes: a fixed case having an internal space formed therein; a pattern plate provided inside the fixed case and provided to calibrate the three-dimensional scanner comprising a camera; a movable case into which at least a portion of the three-dimensional scanner is inserted such that the camera faces the pattern plate, the movable case being configured to move to allow the three-dimensional scanner to move by at least one of rotational movement or vertical movement; and a movement driver configured to provide a driving force to move at least one of the movable case or the pattern plate. The calibration cradle provides an advantage of improving the reliability of calibration and user convenience.

15 Claims, 13 Drawing Sheets

(51) Int. Cl.
A61B 1/24 (2006.01)
A61C 9/00 (2006.01)

(52) U.S. Cl.
CPC .......... A61B 5/0088 (2013.01); A61C 9/0053 (2013.01); A61B 2560/0223 (2013.01); A61B 2560/0456 (2013.01)

(56) References Cited

U.S. PATENT DOCUMENTS

| | | | |
|---|---|---|---|
| 2006/0102833 A1 | 5/2006 | Eiff et al. | |
| 2007/0252911 A1* | 11/2007 | Komiyama | H04N 1/00278 |
| | | | 348/207.1 |
| 2015/0288952 A1 | 10/2015 | Popilka et al. | |
| 2016/0191901 A1 | 6/2016 | Stegall et al. | |
| 2018/0333232 A1 | 11/2018 | Lee | |
| 2020/0103939 A1* | 4/2020 | Hsu | G06F 1/1632 |
| 2021/0045637 A1 | 2/2021 | Chang et al. | |

FOREIGN PATENT DOCUMENTS

| | | | |
|---|---|---|---|
| CN | 110132165 A | 8/2019 | |
| CN | 112074228 A | 12/2020 | |
| EP | 2979059 B1 | 5/2021 | |
| KR | 10-2002-0028133 A | 4/2002 | |
| KR | 10-2015-0082438 A | 7/2015 | |
| KR | 1020180106016 A | 10/2018 | |
| KR | 10-1941001 B1 | 1/2019 | |
| KR | 10-2129383 B1 | 7/2020 | |
| WO | 2014158150 A1 | 10/2014 | |
| WO | WO-2020172161 A1 * | 8/2020 | H04N 23/51 |

OTHER PUBLICATIONS

Korean Office Action dated Oct. 17, 2022 in Korean Application No. 10-2021-0020463.
Korean Final Office Action dated Apr. 21, 2023 in Korean Application No. 10-2021-0020463.
Communication dated Jan. 15, 2026 issued by the State Intellectual Property Office of the P.R.China in application No. 202280014590.6.

* cited by examiner

FIG. 11
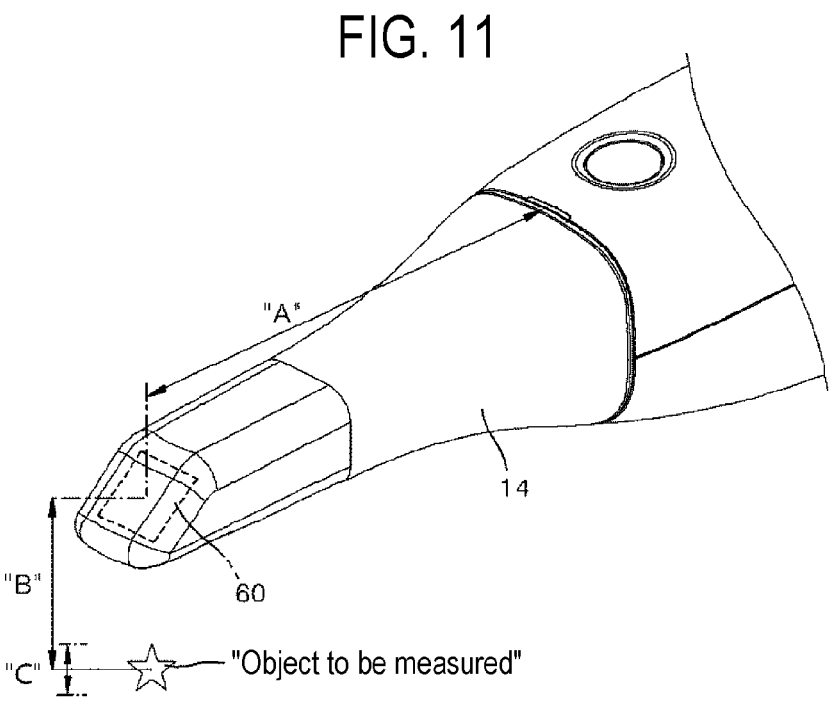
"A"
"B"
"C"
60
14
"Object to be measured"
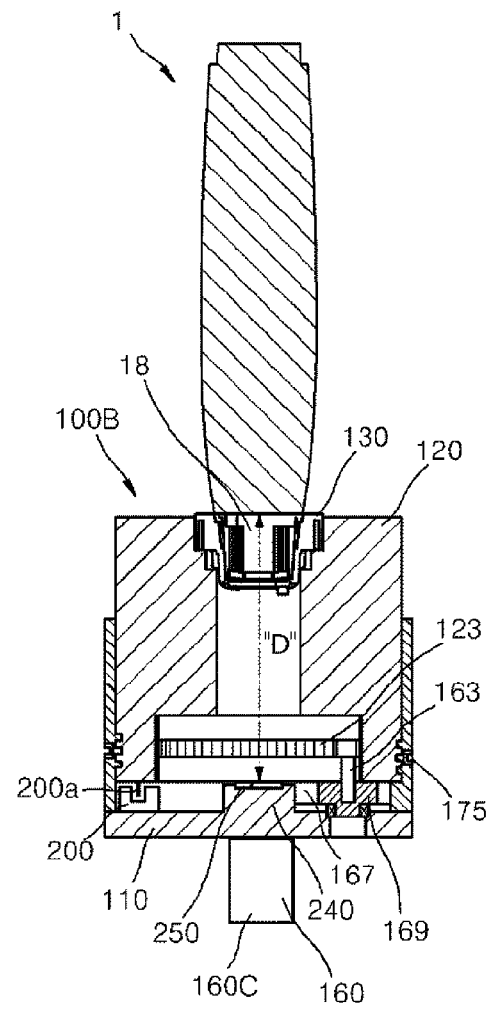
1
18
100B
130    120
"D"
123
163
200a
175
200
110    250    160C    167    240    169    160

CALIBRATION CRADLE FOR THREE-DIMENSIONAL SCANNER

CROSS REFERENCE TO RELATED APPLICATIONS

This application is a National Stage of International Application No. PCT/KR2022/002202 filed Feb. 15, 2022, claiming priority based Korean Patent Application No. 10-2021-0020463 filed Feb. 16, 2021, the entire disclosures of which are incorporated herein by reference.

TECHNICAL FIELD

The present disclosure relates to a calibration cradle for a three-dimensional scanner, and more particularly, to a calibration cradle for a three-dimensional scanner capable of improving calibration accuracy of the three-dimensional scanner and improving user convenience during calibration.

BACKGROUND

An intraoral scanner is a three-dimensional scanner configured to acquire a plurality of optical images of a target object through a series of scanning sequences and to use the optical images to generate three-dimensional model data for the target object. The intraoral scanner refers to a device configured to be suitable for acquiring a series of optical images of a body portion, in particular, a structure inside the oral cavity, such as teeth and gums, among such three-dimensional scanners.

Here, the intraoral scanner may be configured such that a portion of the intraoral scanner (e.g., a probe tip or a tip case provided with a reflective member) is replaceable for hygiene purposes.

In order to acquire accurate three-dimensional model data, error correction work (i.e., calibration) for the intraoral scanner is often required. For this reason, it is common that a calibration tool is provided as a separate accessory to the intraoral scanner.

However, in the case of the conventional intraoral scanner, calibration is performed by allowing all light paths of the scanner including a replaceable probe tip (or tip case) as described above to be accommodated inside an accommodation portion provided in a calibration tool. As a result, since a reversal phenomenon occurs by an optical member provided inside the probe tip (or the tip case), there is a problem in that the accuracy of calibration is degraded. In addition, there is a problem in that calibration accuracy is also degraded when a foreign substance, such as mist or water scale, is generated on the optical member of the probe tip (or tip case).

In addition, when a user performs calibration, it is necessary to manually manipulate a provided pattern plate at various distances and angles, and thus it is difficult to assure calibration accuracy.

SUMMARY

The present disclosure has been made to solve the above-described technical problems, and the present disclosure provides a calibration cradle for a three-dimensional scanner in which the three-dimensional scanner can be inserted into and seated in the calibration cradle in a state in which a tip case including an optical member is removed in order to conduct more accurate calibration of the three-dimensional scanner.

In addition, the present disclosure provides a calibration cradle for a three-dimensional scanner in which a pattern plate is configured to automatically move when the three-dimensional scanner is inserted and seated in order to conduct more accurate calibration of the three-dimensional scanner and to improve user convenience.

The technical problems of the present disclosure are not limited to those mentioned above, and other technical problems not mentioned above will be clearly understood by a person of ordinary skill in the art from the description below.

A calibration cradle for a three-dimensional scanner according to an embodiment of the present disclosure includes: a fixed case having an internal space formed therein; a pattern plate provided inside the fixed case and provided to calibrate the three-dimensional scanner including a camera; a movable case into which at least a portion of the three-dimensional scanner is inserted such that the camera faces the pattern plate, the movable case being configured to move to allow the three-dimensional scanner to move by at least one of rotational movement or vertical movement; and a movement driver configured to provide a driving force to move at least one of the movable case or the pattern plate.

Here, the movable case may be vertically moved by the movement driver, the pattern plate may be disposed inside the fixed case to be inclined to one side and may be rotated by the movement driver, and while the movable case or the pattern plate moves, the angle between an optical axis of light emitted from the three-dimensional scanner to the pattern plate and a rotation axis of the pattern plate may be maintained.

In addition, the movement driver may include a case mover configured to vertically move the movable case, and a pattern mover configured to rotationally move the pattern plate, wherein when the case mover and the pattern mover stop, the camera may operate to conduct calibration, and at least one of the case mover or the pattern mover may move.

In addition, the case mover may include a case driving motor penetrating a movable panel provided in a horizontal direction so as to be connected to the movable case inside the movable case, and at least one panel guide configured to guide the vertical movement of the movable panel.

In addition, at least one of a vertical movement detector configured to detect the vertical movement of the movable case or a pattern rotation detector configured to detect a rotation of the pattern plate may be provided inside the fixed case.

In addition, a seat in which at least a portion of the three-dimensional scanner is seated may be provided on a top surface of the movable case, and a mounting sensor configured to detect the seating of the three-dimensional scanner may be provided in the movable case adjacent to the seat.

In addition, the mounting sensor may be provided in a form of a tact switch that comes into contact with the three-dimensional scanner inserted through the seat.

In addition, the movable case may be rotationally moved and vertically moved by the movement driver, and the pattern plate may be fixed inside the fixed case to be inclined to one side.

In addition, while the movable case rotationally moves and vertically moves, an angle between an optical axis of light emitted from the three-dimensional scanner to the pattern plate and the pattern plate may be maintained.

In addition, the movable case may be provided inside the fixed case to be in contact with an inner peripheral surface of the fixed case, the movement driver may include a case driving motor having a rotation shaft extending vertically toward the movable case, and a guide member extending through the fixed case such that a tip is inserted into a spiral groove formed on an outer peripheral surface of the movable case to guide the rotational movement of the movable case, and the spiral groove may be provided to surround the movable case in a spiral form along an outer peripheral surface of the movable case so that the movable case can simultaneously conduct the rotational movement and the vertical movement.

In addition, the movement driver may include a spur gear connected to and rotated in conjunction with the rotation shaft of the case driving motor, and a spur internal gear formed on an inner peripheral surface of the movable case and meshing with the spur gear.

In addition, the spur internal gear may be formed on an inner peripheral surface of the movable case and may have a vertical height corresponding to a vertical height of the spiral groove.

In addition, the movement driver may include a driving pulley provided at a tip of the rotation shaft of the case driving motor, a spur gear disposed in parallel with the rotation shaft of the case driving motor, a driven pulley coaxially connected to the rotation shaft of the spur gear, and a connection belt configured to rotate by being wound around and meshing with the driving pulley and the driven pulley, wherein the driving pulley, the driven pulley, and the connection belt may be provided in a form of gear-meshing with each other.

The movement driver may be operated by receiving power from a rechargeable battery provided in the fixed case, and the rechargeable battery may be configured to be charged in a wireless or wired manner.

In addition, the three-dimensional scanner may include a light projector configured to emit light, and the light emitted from the light projector may be directly emitted onto the pattern plate without refraction.

In addition, when the three-dimensional scanner is inserted into the movable case in a state in which the tip case including an optical member configured to refract the light is removed, an initial position for the three-dimensional scanner to conduct calibration may be set to vary depending on a distance between the camera and the optical member of the removed tip case.

According to embodiments of the calibration cradle for a three-dimensional scanner according to the present disclosure, the following various effects can be achieved.

First, by removing the tip case portion to be introduced into a patient's oral cavity from the three-dimensional scanner and conducting calibration through the calibration cradle, the accuracy of calibration can be prevented from being degraded due to a foreign substance and an optical member.

Second, by setting the linear reciprocating distance of the pattern plate considering the separation distance between an object to be measured and the optical member of the three-dimensional scanner removed for calibration, calibration reliability can be improved.

Third, since the pattern plate is relatively linearly reciprocated and/or rotated when the three-dimensional scanner is inserted into and seated in the cradle main body, user convenience can be improved.

BRIEF DESCRIPTION OF DRAWINGS

FIG. 3 is a view illustrating a usage state of a calibration cradle for a three-dimensional scanner according to an embodiment of the present disclosure.

FIGS. 9A and 9B illustrate a cutaway perspective view and a cross-sectional view in which an example of a movement driver among the components of FIG. 7 is applied.

FIGS. 10A and 10B illustrate a cutaway perspective view and a cross-sectional view in which another example of the movement driver among the components of FIG. 7 is applied.

FIG. 11 illustrates a perspective view and a cross-sectional view showing an example of a linear reciprocating movement design of a calibration cradle for a three-dimensional scanner according to an embodiment of the present disclosure.

DESCRIPTION OF REFERENCE NUMERALS

Figure 1:
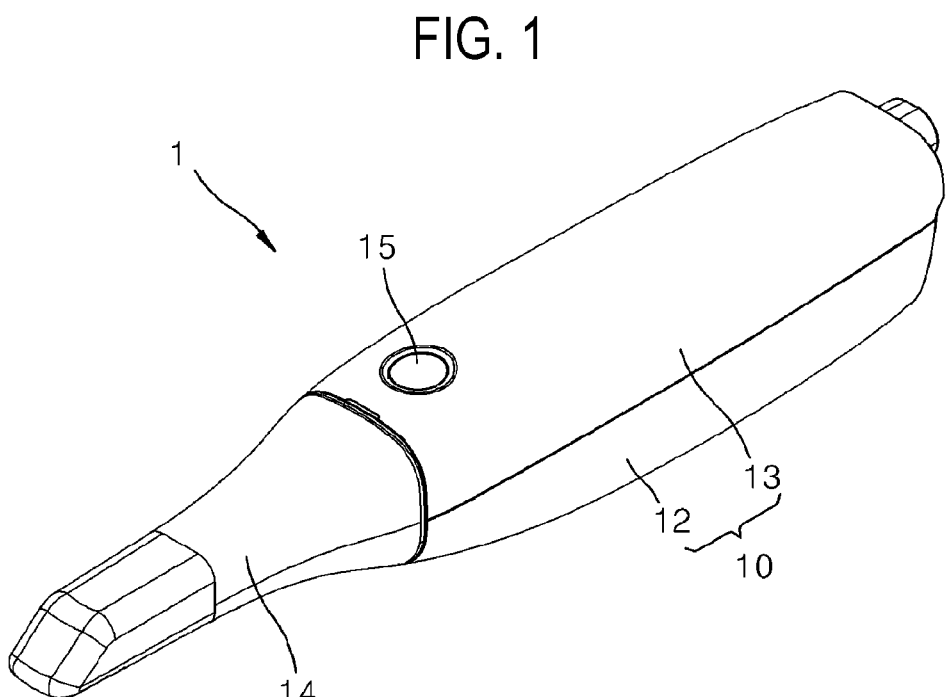
FIG. 1 is a perspective view illustrating an example of a three-dimensional scanner applied to a calibration cradle for a three-dimensional scanner according to the present disclosure.

1: three-dimensional scanner, 18: connection block
100A, 100B: calibration cradle, 110: fixed case
120: movable case, 130: seat
140: mounting sensor, 150: movable panel
160: case driving motor, 170: panel guide
180: stopping nut, 190: guide bush
200: vertical movement detector, 205: movement driver
205A: case mover, 205B: pattern mover
210: pattern rotation detector, 240: installation block
250: pattern plate

DETAILED DESCRIPTION

Hereinafter, embodiments of a calibration cradle for a three-dimensional scanner according to the present disclosure will be described in detail with reference to the accompanying drawings.

In adding reference numerals to components of each drawing, it is to be noted that the same components have the same numeral, if possible, even when the components are illustrated on different drawings. In addition, in describing the embodiments of the present disclosure, a detailed description on known configurations or functions related thereto will be omitted when it is determined that the detailed description may hinder understanding of the embodiments of the present disclosure.

In describing a component of the embodiments of the present disclosure, terms, such as first, second, A, B, (a), and (b) may be used. These terms are only used to distinguish the component from other components, and the nature, sequence, or order of the corresponding component is not limited by the terms. In addition, unless defined otherwise, all terms used herein, including technical or scientific terms, have the same meaning as commonly understood by a person of ordinary skill in the art to which the present disclosure belongs. Terms such as those defined in a commonly used dictionary should be interpreted as having a meaning consistent with the meaning in the context of the related art, and unless explicitly defined in the present application, the terms should not be interpreted in an ideal or overly formal sense.

Figure 2:
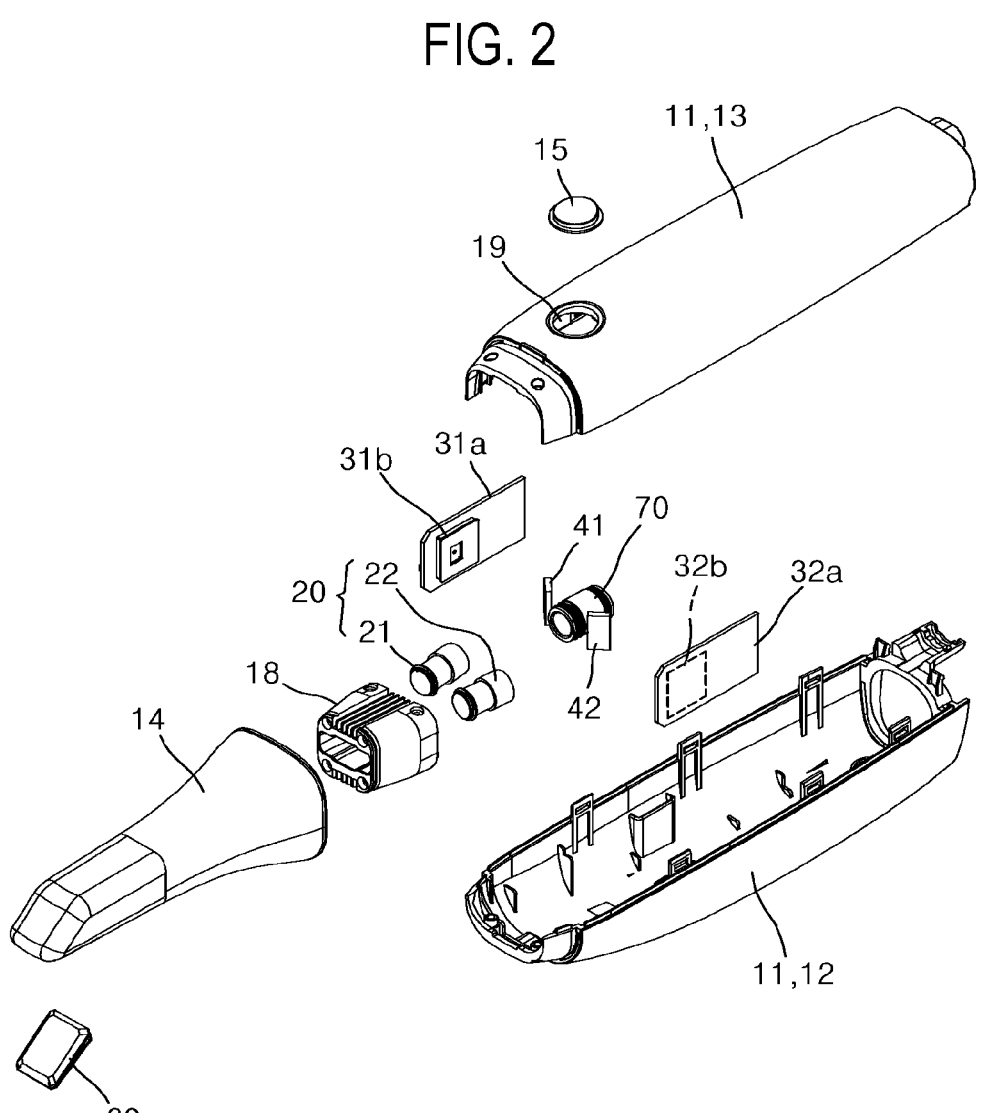
FIG. 2 is an exploded perspective view of FIG. 1.

FIG. 1 is a perspective view illustrating an example of a three-dimensional scanner applied to a calibration cradle for a three-dimensional scanner according to the present disclosure, and FIG. 2 is an exploded perspective view of FIG. 1.

First, an example of a three-dimensional scanner 1 to be applied to a calibration cradle 100 for a three-dimensional scanner according to the present disclosure will be described in detail with reference to the drawings.

As illustrated in FIGS. 1 and 2, the three-dimensional scanner 1 applied to the calibration cradle for a three-dimensional scanner according to an embodiment of the present disclosure may include a main body case 10 and a tip case 14 which may be coupled to the main body case 10.

Inside the main body case 10, a camera 20 may be disposed. The tip case 14 may have, through one end thereof, an opening 16 which opens to allow an image to be introduced into the inside in the form of light. The opening 16 may be an entrance through which external light is introduced into the tip case 14. Light incident through the opening 16 passes through the camera 20. When light passes through the camera 20, an image is captured through imaging sensors 31b and 32b provided on imaging boards 31a and 32a, which will be described later.

Although not specifically illustrated, the camera 20 may include at least two transmissive lenses capable of adjusting a focus of an image.

To this end, an example of the three-dimensional scanner 1 according to the present disclosure may further include imaging boards 31a and 32a, which have imaging sensors 31b and 32b, respectively, to image-process the light passing through the camera 20. In addition, although not illustrated in the drawings, an embodiment of the three-dimensional scanner 1 according to the present disclosure may further include a camera control board equipped with electrical components for controlling the operation of the camera 20 and a scanning control board equipped with electrical components for processing scanned images.

As illustrated in FIGS. 1 and 2, the main body case 10 serves to provide a predetermined space such that a number of electrical components, such as the aforementioned camera 20, imaging boards 31a and 32a, a camera control board (not illustrated), and a scanning control board (not illustrated), are embedded.

More specifically, as illustrated in FIG. 2, the main body case 10 may include a lower case 12 that provides a predetermined space in which the aforementioned components are embedded, and an upper case 13 provided on the upper side of the lower case 12 and detachably coupled to the lower case 12 to cover the aforementioned components.

Light incident into the main body case 10 through the opening 16 means "incident light," and light emitted from the interior of the main body case 10 through the opening 16 means "irradiation light" radiated from a light projector 70, which will be described later, as "emission light."

The internal structure of the tip case 14 may be formed as a light guide structure through which the incident light and the emission light are easily radiated to the interior and exterior of the main body case 10. In addition, the opening 16 may be formed to be opened in one direction orthogonal to the longitudinal direction of the tip case 14, and an optical member 60 to be described later may be disposed in the opening 16.

As illustrated in FIG. 2, a connection block 18 may be further provided between the front end of the main case 10 and the rear end of the tip case 14. The connection block 18 may play a role of stably conducting calibration by being inserted into and placed in the calibration cradle 100 to be described later.

On the other hand, as illustrated in FIG. 2, an embodiment of the three-dimensional scanner 1 according to the present disclosure may further include a light projector 70 disposed inside the main body case 10 and configured to radiate emission light through the opening 16 formed at one end of the tip case 14.

The emission light radiated from the light projector 70 is refracted through the optical member 60 of the tip case 14 and emitted to an object to be measured, and at the same time, the emission light reflected on the object to be measured is incident through the optical member 60 of the tip case 14 in the form of incident light, passes through the camera 20 provided inside the main body case 10, and is image-processed by the imaging sensors 31b and 32b of the imaging boards 31a and 32a. Here, the optical member 60 provided in the tip case 14 may be configured with either a prism or a mirror.

Figure 3:
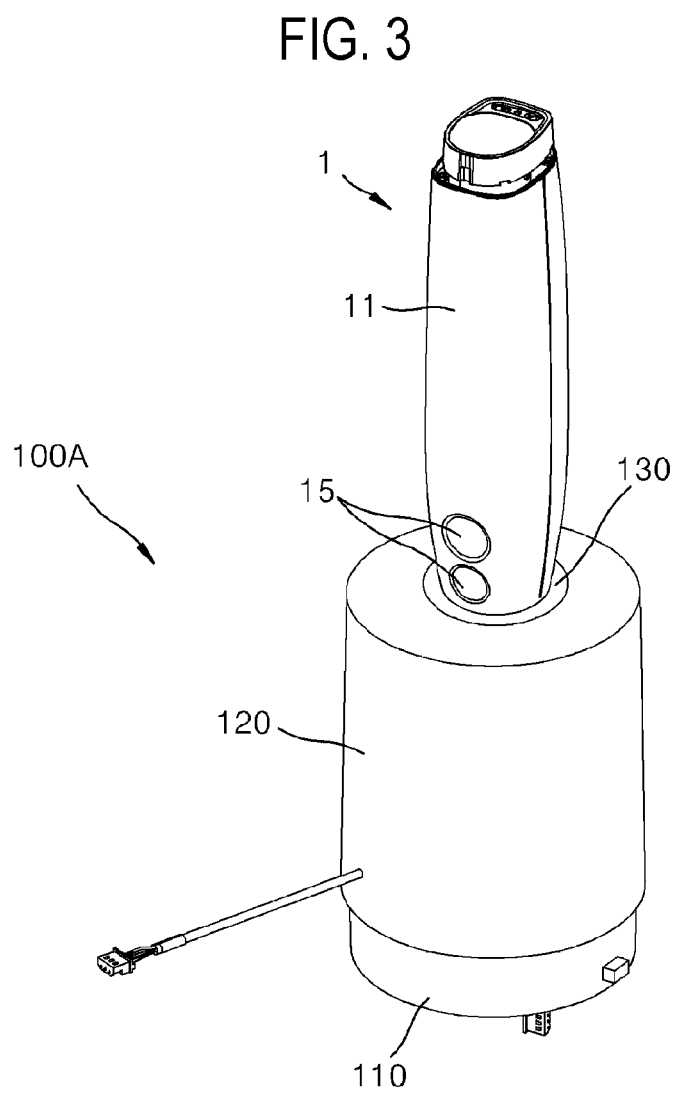
Figure 4:
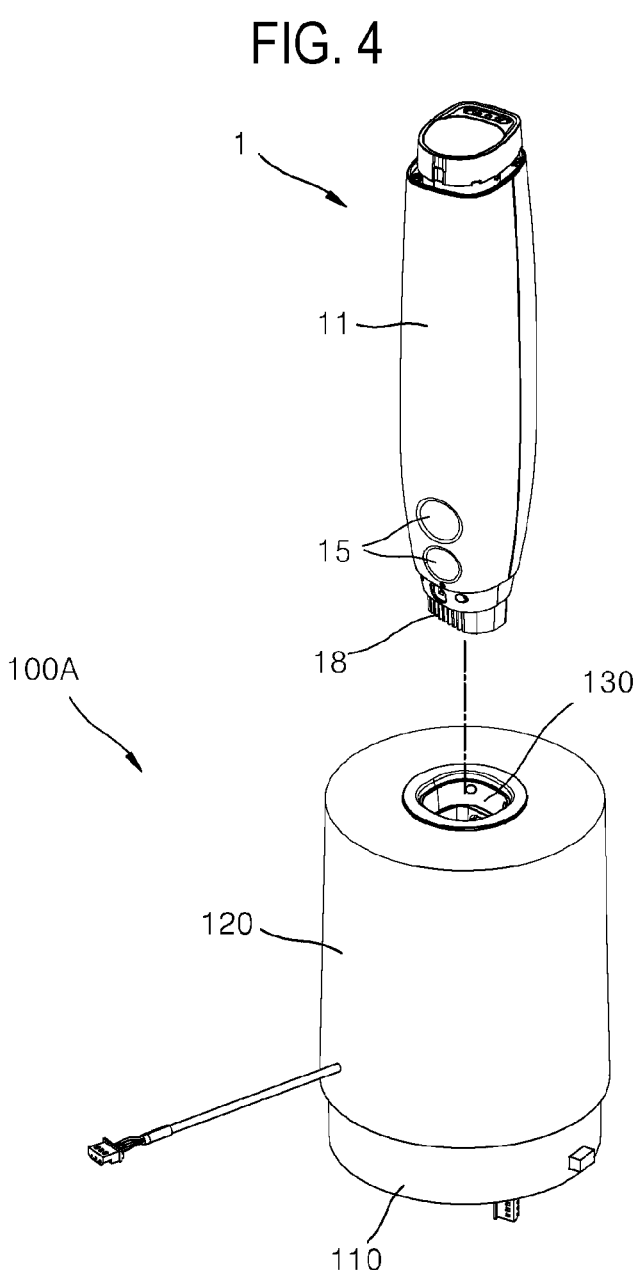
FIG. 4 is an exploded perspective view illustrating a state in which the three-dimensional scanner of FIG. 3 is separated.
Figure 5:
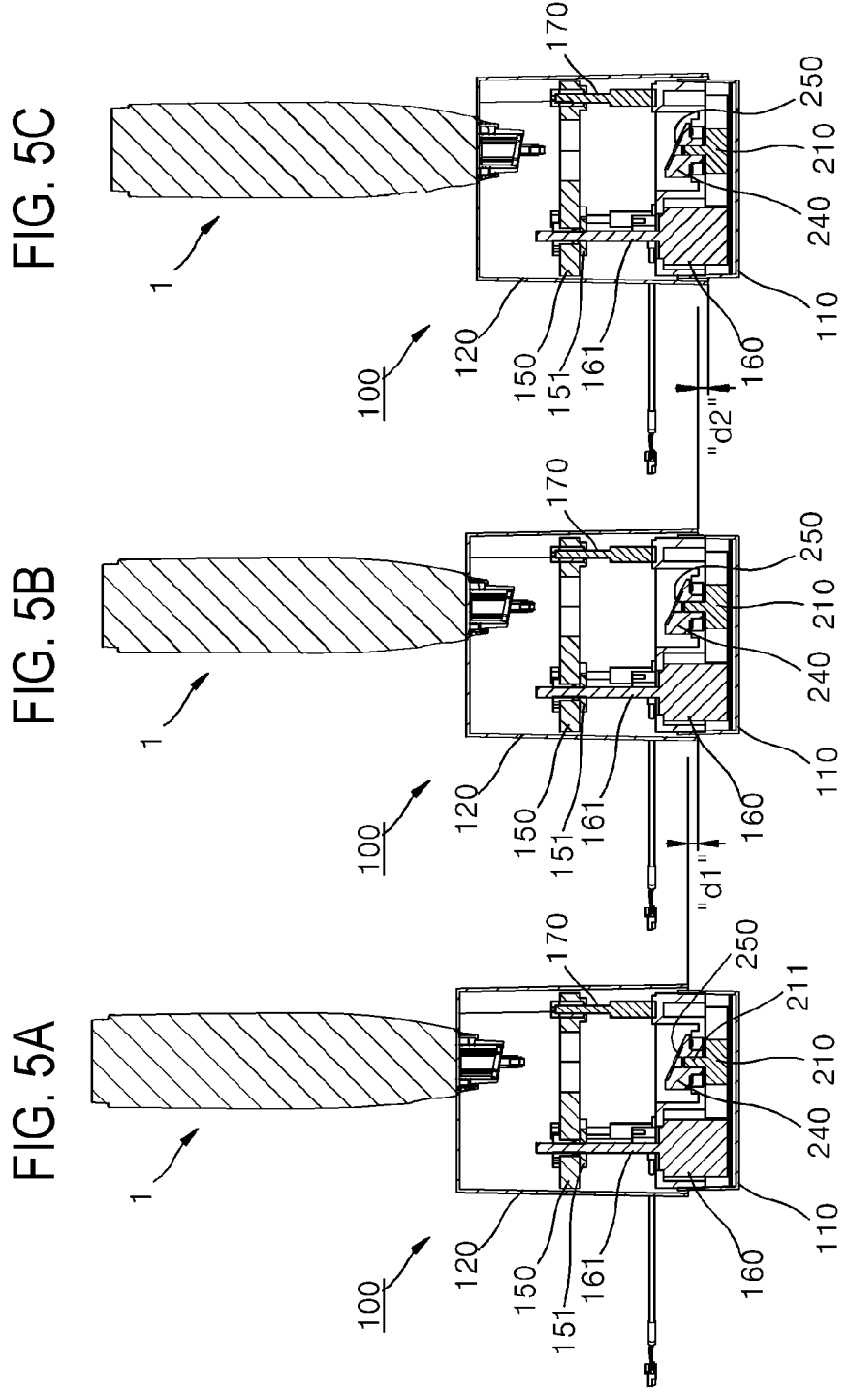
FIGS. 5A to 5C are a cross-sectional view illustrating an action and effect of the calibration cradle for a three-dimensional scanner according to an embodiment of the present disclosure.
Figure 6:
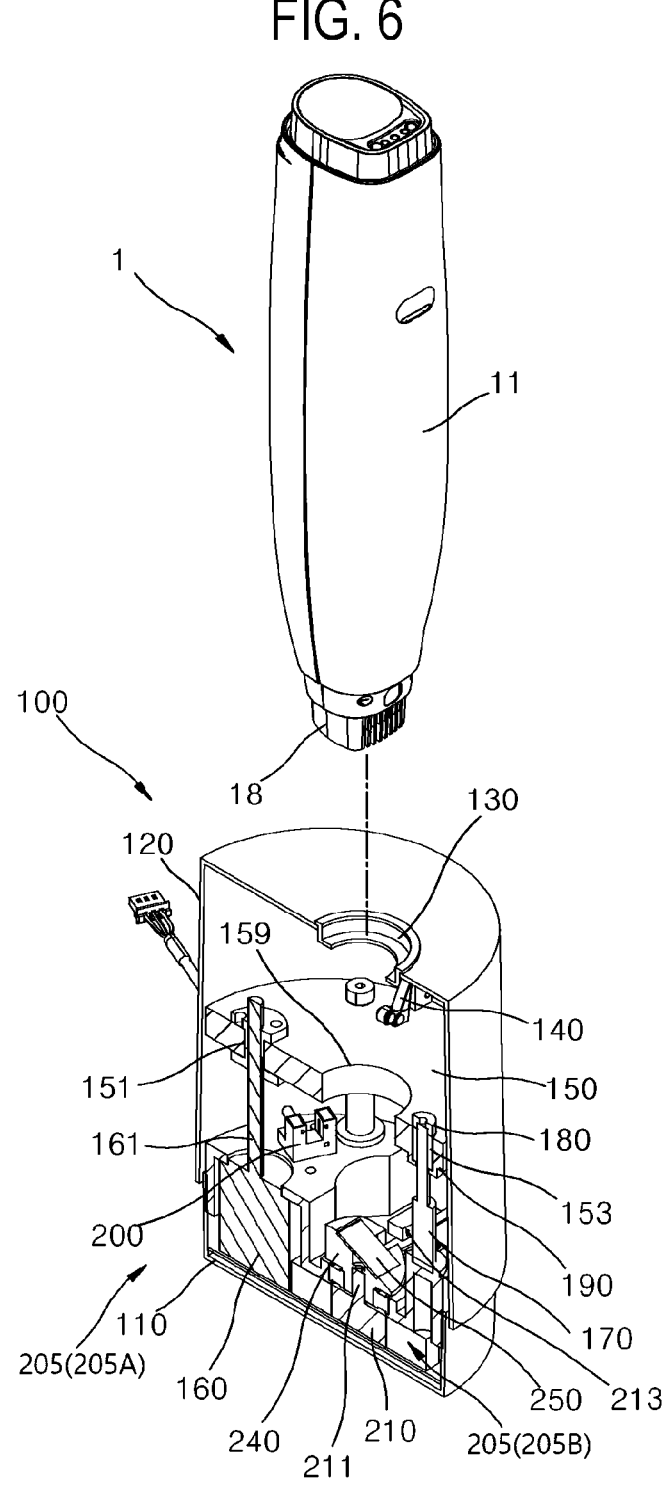
FIG. 6 is a cutaway perspective view of FIG. 3.

FIG. 3 is a view illustrating a usage state of a calibration cradle for a three-dimensional scanner according to an embodiment of the present disclosure, FIG. 4 is an exploded perspective view illustrating a state in which the three-dimensional scanner of FIG. 3 is separated, FIGS. 5A to 5C are a cross-sectional view illustrating an action and effect of the calibration cradle for a three-dimensional scanner according to an embodiment of the present disclosure, and FIG. 6 is a cutaway perspective view of FIG. 3.

An embodiment 100A of a calibration cradle for a three-dimensional scanner according to the present disclosure relates to a calibration cradle dedicated to the three-dimensional scanner described with reference to FIGS. 1 and 2. In particular, the three-dimensional scanner 1 in which calibration is conducted through the calibration cradle 100A in the present embodiment is freely portable by a user, and the front end portion of the tip case 14 is inserted into the oral cavity of a patient so that scanning is conducted through the optical member 60 provided inside the tip case 14.

More specifically, in an example of the aforementioned three-dimensional scanner 1, in order to easily scan the interior of a patient's narrow oral cavity, the optical member 60 is provided to enable easy scanning by refracting emission light radiated from the light projector 70 and incident light in the form of light reflected from the emission light. However, when a foreign substance such as oral moisture of a patient adheres to the optical member 60 when scanning the patient's oral cavity using the three-dimensional scanner 1, it may be impossible to conduct accurate calibration. Therefore, in order to minimize the negative effect of the optical member 60, an embodiment 100A of the calibration cradle for a three-dimensional scanner according to the present disclosure provides a dedicated cradle 100A for only the three-dimensional scanner 1 in a state in which the tip case 14 including the optical member 60 is separated.

As illustrated in FIGS. 3 to 6, an embodiment 100A of the calibration cradle for a three-dimensional scanner according to the present disclosure includes a fixed case 110 having an internal space formed therein, and a movable case 120 coupled to an upper portion of the fixed case 110 to relatively rotate or vertically move relative to the fixed case 110 and configured to form a darkroom with the fixed case 110.

Here, in the upper portion of the movable case 120, a seat 130 into which the front end portion of the three-dimensional scanner 1 (more specifically, the portion into which the tip case 14 is fitted) is inserted in a state in which the tip case 14 including the optical member 60 is removed may be provided.

The seat 130 may be provided to allow the internal space and the external space formed by the movable case 120 to communicate with each other, and serves to ensure that the three-dimensional scanner 1 is stably and vertically mounted on the upper portion of the movable case 120 without shaking in the process of conducting calibration. Therefore, it is preferable for the seat 130 to have a shape that allows the connection block 18 provided at the lower end of the three-dimensional scanner 1 to be firmly mated therewith.

When the tip case 14 is removed, the connection block 18 may be exposed to protrude by a predetermined length from the lower end of the main body case 10. Here, the seat 130 has a shape capable of accommodating the connection block 18 protruding from the lower end of the main body case 10.

In addition, although not illustrated in the drawings, an insertion setting protrusion for setting an insertion position of the connection block 18 may be provided to protrude in the seat 130. The insertion setting protrusion protrudes in the form of a rib inside the seat 130 and may have any shape, but may have a structure configured to prevent the connection block 18 of the three-dimensional scanner 1 from moving in the state of being inserted into and seated in the seat 130.

On the other hand, at the lower end of the main body case 10 of the three-dimensional scanner 1 provided with the connection block 18, an insertion setting groove (not illustrated) to be mated with the insertion setting protrusion provided on the seat 130 may be provided. More specifically, the insertion setting groove may be disposed below the front end portion of the lower case 12 of the main body case 10 of the three-dimensional scanner 1.

The three-dimensional scanner 1 may be coupled when the insertion setting groove provided at the lower end of the main body case 10 and the insertion setting protrusion provided in the seat 130 are mated with each other. Therefore, it is possible for a user who conducts calibration to identify the position of the insertion setting groove provided in the three-dimensional scanner 1 and the insertion setting protrusion provided in the calibration cradle 100A of the present embodiment so that the connection block 18 of the three-dimensional scanner 1 can be inserted into, seated, and coupled to the correct position, and the three-dimensional scanner 1 can be vertically supported such that the optical axis is stably maintained in the process of conducting calibration. By maintaining the optical axis by stably and vertically maintaining the three-dimensional scanner 1, the reliability of calibration can be improved.

Here, the aforementioned optical axis is maintained while the movable case 120 or a pattern plate 250 moves up and down. More specifically, while the movable case 120 or the pattern plate 250 described later moves, the angle between the pattern plate 250 or the rotation axis of the pattern plate 250 and the optical axis of light radiated from the three-dimensional scanner 1 to the pattern plate 250 can be maintained.

The seat 130 into which the three-dimensional scanner 1 is inserted and seated may be located at a position that is spaced apart from the center of the movable case 120 depending on the position of the movement driver 205 or the movement manner of the movable case 120, which will be described later.

Meanwhile, a mounting sensor (see reference numeral 140 in FIG. 6) may further be provided inside the movable case 120 adjacent to the seat 130 to detect insertion and seating of the three-dimensional scanner 1.

The mounting sensor 140 is provided in the form of a tact switch, and an electrical signal may be switched when the connection block 18 of the three-dimensional scanner 1, which is inserted through the seat 130, comes into contact with the mounting sensor 140. To this end, the mounting sensor 140 is preferably installed in the movable case 120 at a portion adjacent to the seat 130.

When the insertion and seating of the three-dimensional scanner 1 is detected via the mounting sensor 140, the operation of the calibration cradle 100A for a three-dimensional scanner according to an embodiment of the present disclosure is prepared (stand-by), and when a predetermined time elapses in the stand-by state, calibration may be automatically conducted.

In addition, although not illustrated in the drawings, an illuminance sensor configured to detect predetermined light may be further provided inside the fixed case 110 or the movable case 120. When the three-dimensional scanner 1 operates and the predetermined light is radiated from the light projector 70 to the internal space forming a darkroom, the illuminance sensor may detect the light and may present a criterion for determining a time point at which the movement driver 205 to be described later is capable of operating.

On the other hand, as illustrated in FIGS. 3 to 6, at least one of a vertical movement detector (see reference numeral 200 in FIG. 6) configured to detect the vertical movement of the movable case 120 or a pattern rotation detector (see reference numeral 213 in FIG. 6) configured to detect the rotation of the pattern plate 250 may be provided in the fixed case 110. The pattern rotation detector may not be provided when a pattern driving motor 210 is configured with a stepping motor. That is, since the stepping motor is provided to be rotated by a set amount depending on pulses, a separate pattern rotation detector is not required. When the three-dimensional scanner 1 stops after rotating by the operation of the pattern driving motor 210 configured with a stepping motor, the camera 20 of the three-dimensional scanner 1 may operate. Here, the process from rotation to stopping of the three-dimensional scanner 1 may be performed multiple times (e.g., 9 times in total) from the initial position to the completion position of the calibration, and the operation of the camera 20 for conducting the calibration may also be performed the same number of times.

The vertical movement detector is provided in the internal space of the fixed case 110 in the fixed state and serves to detect the relative distance of the movable case 120, which is moved vertically by the operation of a case driving motor 160, relative to the fixed case 110. In addition, the pattern rotation detector is provided in the internal space of the fixed case 110 in the fixed state and serves to detect the rotation of the pattern plate 250 rotated around an axis by the operation of the pattern driving motor 210.

Based on the positional information of the movable case 120 and the pattern plate 250 obtained via the vertical movement detector and the pattern rotation detector performing the aforementioned functions, it is possible to determine whether the movable case and the pattern plate are returned to their initial positions at the time of calibration.

The vertical movement detector and the pattern rotation detector may include one of a photo sensor unit and a Hall sensor unit.

For example, when the vertical movement detector is a photo sensor unit, as illustrated in FIG. 6, the photo sensor unit may include a photo sensor 200 fixed to the bottom surface of the fixed case 110 and a detection lead (not illustrated) provided on the bottom surface of the movable panel 150 provided in the horizontal direction inside the movable case 120.

In addition, when the pattern rotation detector is the photo sensor unit, as illustrated in FIG. 6, the photo sensor unit may include a photo sensor 213 fixed to one side of the pattern plate 250 of the fixed case 110 (since a component similar to a photo sensor in 3D is illustrated, a pattern rotation detector is employed and illustrated) and a detection lead (not illustrated) provided to move in conjunction with the pattern plate 250. Here, the detection lead may be fixed to a portion of the outer peripheral surface of an installation block 240 on which the pattern plate 250 is installed to be inclined and may rotate in conjunction with the pattern plate 250.

Similarly, when the vertical movement detector 200 is a Hall sensor unit, although not illustrated in the drawings, the Hall sensor unit may include a Hall sensor fixed to the bottom surface of the fixed case 110 and a detection magnet provided on the bottom surface of the movable panel 150 and linearly moved in conjunction with the movable case 120.

In addition, when the pattern rotation detector is a Hall sensor unit, although not illustrated in the drawings, the Hall sensor unit may include a Hall sensor fixed to the fixed case 110 and at least one detection magnet provided on the outer peripheral surface of the installation block 240 on which the pattern plate 250 is installed.

Meanwhile, the fixed case 110 and the movable case 120 may be mutually mated with each other to form a predetermined darkroom where external light does not enter during the calibration process. In the state in which the darkroom is formed, the movable case 120 into which the three-dimensional scanner 1 is inserted and seated can be relatively rotated or vertically moved relative to the fixed case 110 to change the relative distance between the pattern plate 250 and the three-dimensional scanner 1 so that calibration can be conducted with more accurate reliability.

In the internal space formed by the fixed case 110 and the movable case 120, an irradiation path of emission light and incident light radiated from the light projector 70 of the three-dimensional scanner 1 may be provided. In particular, the irradiation path of the emission light and the incident light may be provided in the form of a darkroom so as to prevent external light from being affected by external light. That is, when the three-dimensional scanner 1 is inserted into and seated in the seat 130, the internal space formed by the fixed case 110 and the movable case 120 forms a darkroom in which no light exists, and when the light projector 70 of the three-dimensional scanner 1 is operated to conduct calibration, only the emission light radiated from the light projector 70 and the incident light in the form of reflected light reflected from the pattern plate 250 exist inside the darkroom. At this time, the light emitted from the light projector 70 is obtained by removing the tip case 14 including the optical member 60 from the three-dimensional scanner 1 and may be directly radiated to the pattern plate 250 to be described later without refraction.

As referred to in FIGS. 3 to 6, since the movable case 120 is linearly moved in the vertical direction with respect to the fixed case 110 to change the relative distance between the three-dimensional scanner 1 and the pattern plate 250 (to be described later) and the pattern plate 250 (to be described later) disposed to have a predetermined inclination is rotated about an axis, an embodiment 100A of the calibration cradle for a three-dimensional scanner according to the present disclosure is implemented to conduct calibration more quickly by using a single pattern plate 250.

For reference, another embodiment 100B of the calibration cradle for a three-dimensional scanner according to the present disclosure illustrated in FIGS. 7 to 10B is different from the above-described embodiment in that the present embodiment is implemented to conduct calibration while making the movable case 120 simultaneously conduct relative rotation and vertical rotation relative to the fixed case 110 in the state in which the pattern plate 250 is fixed inside the fixed case 110. This will be described in more detail later.

On the other hand, as illustrated in FIGS. 3 to 6, the embodiment 100A of a calibration cradle for a three-dimensional scanner according to the present disclosure may further include a movement driver 205 provided inside the fixed case 110 and configured to provide a predetermined driving force to each of the calibrating pattern plate (hereinafter, simply referred to as a "pattern plate") 250 and the movable case 120, which are configured to conduct scanning correction for the three-dimensional scanner 1, to relatively rotate or vertically move each of the calibrating pattern plate 250 and the movable case 120 relative to the fixed case 110. Here, the movement driver 205 may serve to provide a driving force such that at least one of the movable case 120 or the pattern plate 250 moves.

As illustrated in FIGS. 3 to 6, on the outer surface of the pattern plate 250, predetermined patterns (not denoted with reference numerals) may be printed or provided to obtain calibration data through scanning by the three-dimensional scanner 1. As illustrated in FIGS. 5A to 6, such a pattern plate 250 may be disposed to be inclined on the top surface of the installation block 240 in which the top surface is inclined at a predetermined angle. The inclination angle of the pattern plate 250 may be set to be 40 degrees or more and less than 50 degrees with reference to the vertical direction in which the optical axis is formed. When the pattern plate 250 is provided to be orthogonal (i.e., 90 degrees) to the vertical direction of the optical axis, there is a disadvantage in that each of the patterns formed on the pattern plate 250 has the same depth information (or height information) with respect to the same surface. In the embodiments of the present disclosure, the pattern plate 250 is disposed to be inclined at a predetermined angle relative to the vertical direction of the optical axis to increase a calibration effect.

Here, as illustrated in FIG. 6, the movement driver 205 may include a case mover 205A configured to vertically move the movable case 120 and a pattern mover 205B configured to rotate the pattern plate 250.

The case mover 205A may include at least any one of a case driving motor 160, an axial bearing 151, or a panel guide 170.

More specifically, as illustrated in FIGS. 5A to 6, the case driving motor 160 may include a rotation shaft 161 provided inside the movable case 120 to vertically penetrate the movable panel 150 provided in a horizontal direction to be connected to the movable case 120. In addition, the axial bearing 151 may be interposed such that the rotation shaft of the case driving motor 160 penetrates the penetrating portion in the movable panel 150 and may mesh with a spiral groove (not illustrated) formed in the outer peripheral surface of the rotation shaft 161 of the case driving motor 160. In addition, the panel guide 170 may be disposed to vertically penetrate the movable panel 150 and guide the vertical movement of the movable panel 150.

Here, the movable panel 150 provided in the movable case 120 may be provided to completely partition the internal space formed with the fixed case 120 in the horizontal direction except for a light path of emission light and incident light in the above-described three-dimensional scanner 1. The above-described light path is located on an optical axis for conducting calibration, and for this purpose, a light path hole 159 may vertically penetrate the movable panel 150.

At least one panel guide 170 may be a guide rod having a lower end portion fixed to the fixed case 110 and an upper end portion penetrating the movable panel 150 to be exposed upward.

A guide bush 153 may be interposed between the panel guide 170 and the penetrating portion of the movable panel 150 to minimize frictional force when the movable panel 150 moves up and down.

In addition, a stopping nut 180 may be fixed to the upper end of the panel guide 170. The stopping nut 180 may serve to limit an upward moving distance of the movable panel 150.

On the other hand, although not illustrated in detail in the drawings, the rotation shaft 161 of the case driving motor 160 may be configured with a screw rod in which a spiral groove vertically extends in a certain portion. A bearing ball (not illustrated) of the axial bearing 151 fixed to the penetrating portion of the movable panel 150 may mesh with the spiral groove formed in the rotation shaft 161 of the case driving motor 160 to allow the rotation shaft 161 of the case driving motor 160 to linearly move upward or downward depending on the rotation direction of the rotation shaft 161 of the case driving motor 160.

As illustrated in FIGS. 5A to 6, the pattern mover 205B may be fixed to the lower portion of the fixed case 110 and may include a pattern driving motor 210 having a rotation shaft 211 vertically fixed to the lower portion of the installation block 240 on which the pattern plate 250 is installed to be inclined. That is, the pattern plate 250 may be disposed to be inclined to one side via the installation block 240 located inside the fixed case 110 and may be rotationally moved around a vertical axis by the pattern driving motor 210 of the pattern mover 205B among the components of the movement driver 205.

Meanwhile, although not illustrated in the drawings, a rechargeable battery configured to supply power to the movement driver 205 may be further provided in the internal space of the fixed case 110, and the rechargeable battery may be charged in a wired or wireless manner. Accordingly, the portability and usability of the embodiment 100A of the calibration cradle for a three-dimensional scanner according to the present disclosure can be greatly improved.

An operation process of the calibration cradle 100A for a three-dimensional scanner according to an embodiment of the present disclosure configured as described above will be briefly described with reference to the accompanying drawings (particularly, FIGS. 5A to 5C). However, the position of the three-dimensional scanner 1 will be described considering that the position has already been set and located at the initial position for conducting calibration.

First, as illustrated in FIG. 5A, after the three-dimensional scanner 1 is inserted into and seated in the upper portion of the movable case 120, when the case driving motor 160 of the case mover 205A among the components of the movement driver 205 is rotated in one direction, the movable case

120 into which the three-dimensional scanner 1 is inserted and seated moves downward in conjunction with each other while the movable panel 150 moves linearly downward due to the interaction between the rotation shaft 161 of the case driving motor 160 and the axial bearing 151.

At this time, as illustrated in FIG. 5B, by the operation in which the rotation shaft 211 of the pattern driving motor 210 of the pattern mover is rotated in one direction by 360 degrees, the pattern plate 250 can be rotationally moved once, and the movable case 120 can be linearly moved downward by "d1."

Further, as illustrated in FIG. 5C, when the rotation shaft 161 of the case driving motor 160 is continuously rotated in one direction among the component of the case mover and the rotation shaft 211 of the pattern driving motor 210 among the components of the pattern mover is rotated in one direction once by 360 degrees, the movable case 120 can be moved linearly downward again by "d2."

Here, the camera 20 of the three-dimensional scanner 1 may be operated to conduct calibration during the process of stopping the case mover 205A and the pattern mover 205B of the movement driver 205. The process of stopping the case mover 205A and the pattern mover 205B may be repeated several times (e.g., 9 times in total) from the initial position to the completion position of the calibration, and it is possible to obtain more calibration data by changing the relative distance and relative rotation angle between the camera 20 and the pattern plate 250.

As described above, with the calibration cradle 100A for a three-dimensional scanner according to an embodiment of the present disclosure, calibration based on various data may be conducted while continuously changing the relative distance (light path distance) between the three-dimensional scanner 1 and the pattern plate 250 and the pattern depth difference of the pattern plate 250 by the case mover and the pattern mover.

However, in changing the relative distance (light path distance) between the three-dimensional scanner 1 and the pattern plate 250 and the pattern depth of the pattern plate 250, the movement driver 205 does not necessarily have to be provided separately as the case mover 205A and the pattern mover 205B as in the above-described embodiment 100A. The same calibration effect can be achieved by driving only the movable case 120 to relatively rotate and vertically move relative to the fixed case 250 while the pattern plate 250 is fixed inside the fixed case 110 as in the calibration cradle 100B for a three-dimensional scanner according to another embodiment of the present disclosure to be described below.

Figure 7:
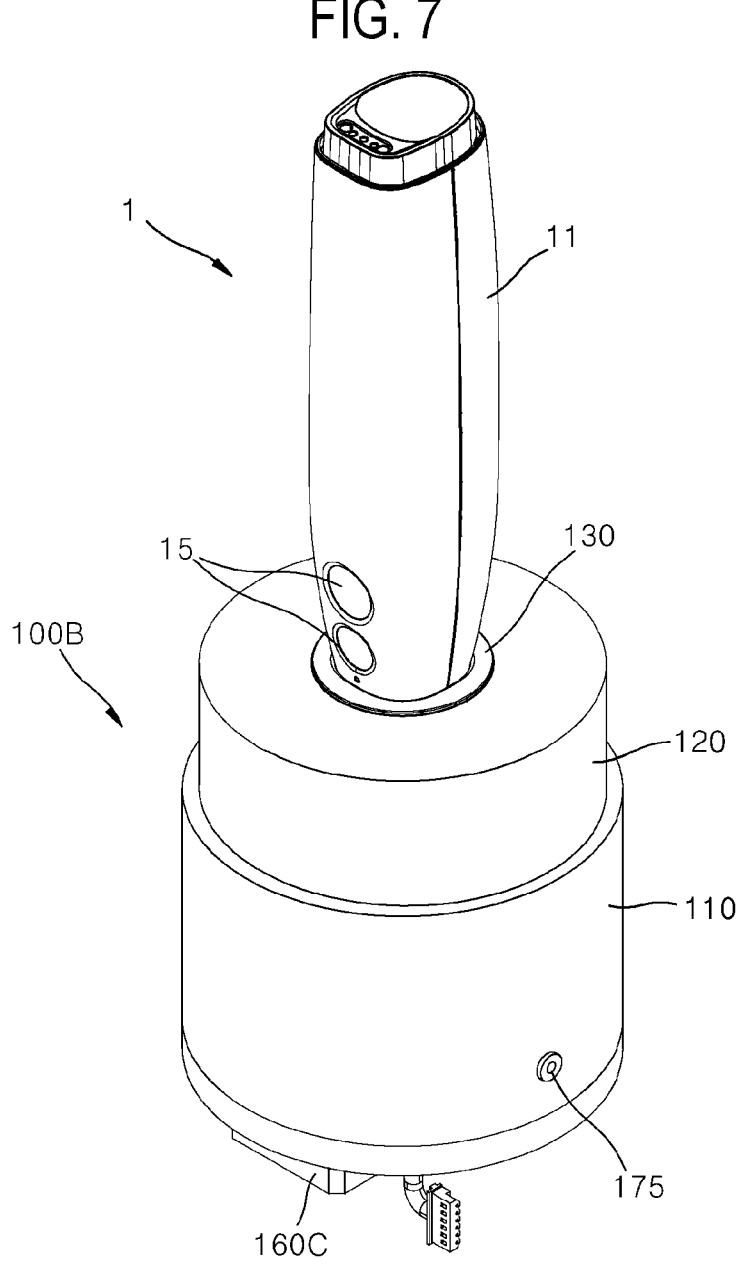
FIG. 7 is a view illustrating a usage state of a calibration cradle for a three-dimensional scanner according to another embodiment of the present disclosure.
Figure 8:
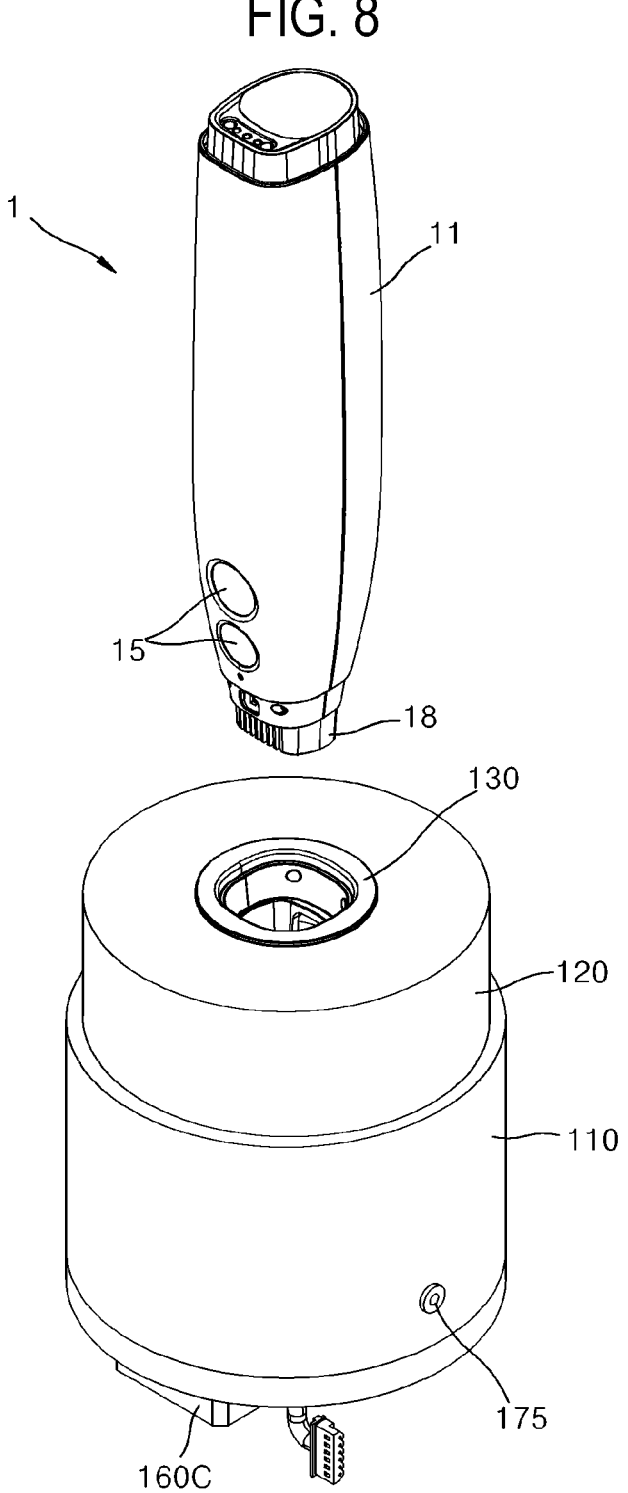
FIG. 8 is an exploded perspective view illustrating a state in which the three-dimensional scanner of FIG. 7 is separated.
Figure 9A:
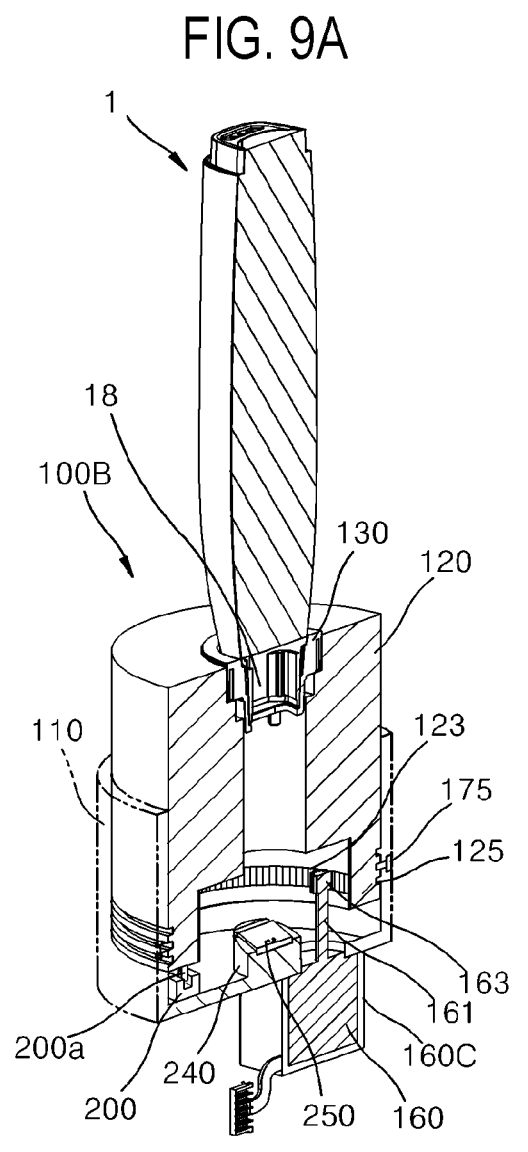
Figure 9B:
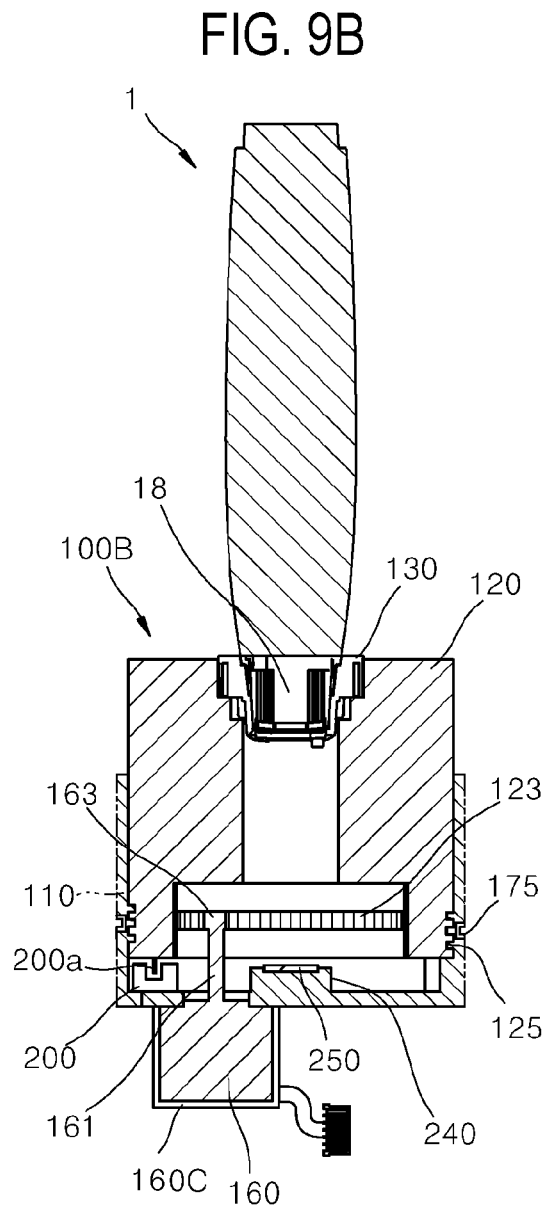
Figure 10A:
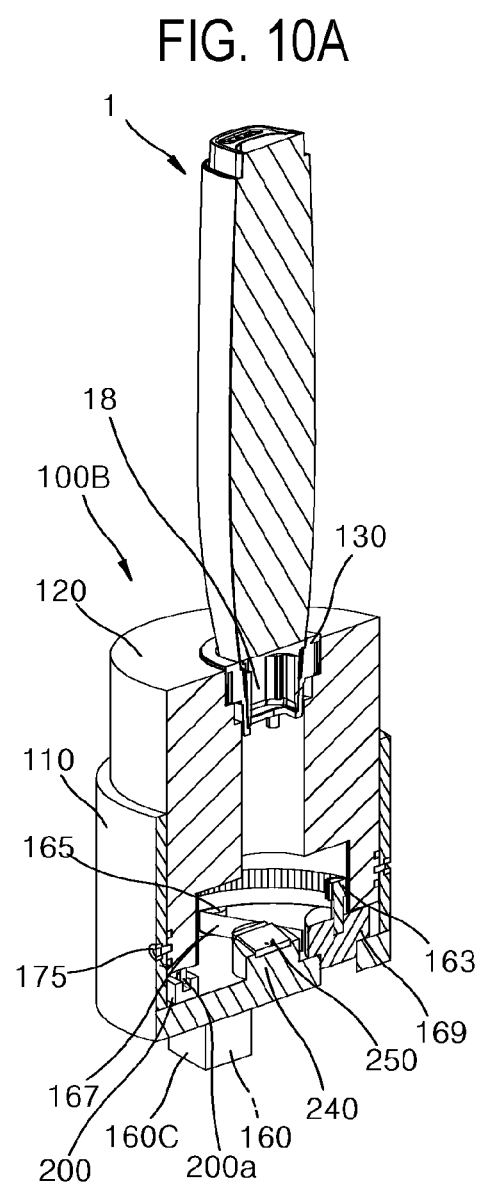
Figure 10B:
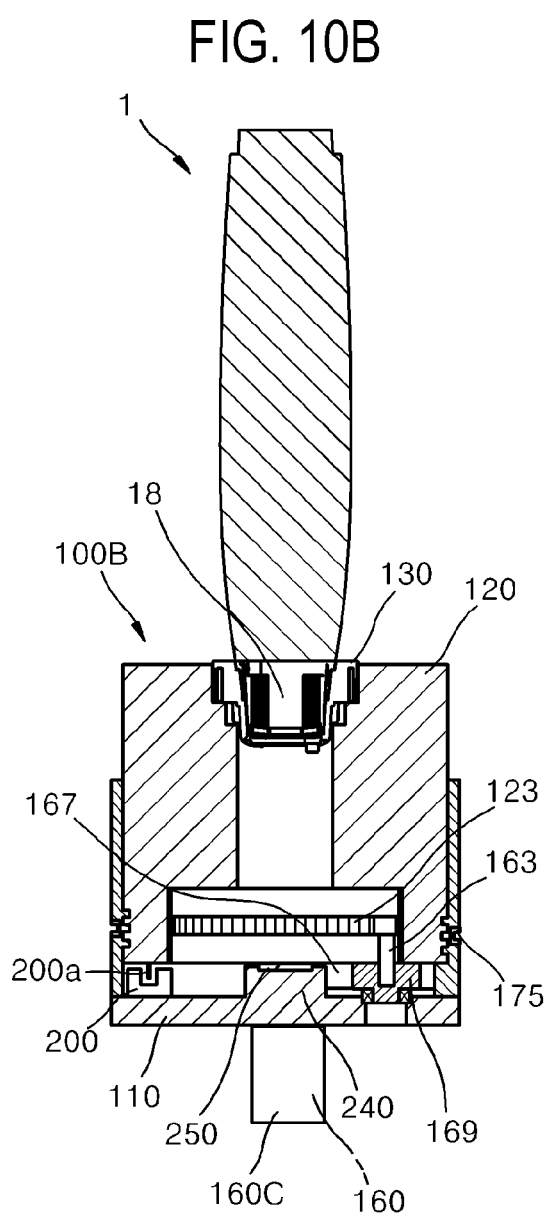

FIG. 7 is a view illustrating a usage state of a calibration cradle for a three-dimensional scanner according to another embodiment of the present disclosure, FIG. 8 is an exploded perspective view illustrating a state in which the three-dimensional scanner of FIG. 7 is separated, FIGS. 9A and 9B illustrate a cutaway perspective view and a cross-sectional view in which an example of the movement driver among the components of FIG. 7 is applied, and FIGS. 10A and 10B illustrate a cutaway perspective view and a cross-sectional view in which another example of the movement driver among the components of FIG. 7 is applied.

Hereinafter, a calibration cradle 100B for a three-dimensional scanner according to another embodiment of the present disclosure will be described in detail, but a description of components overlapping those of the above-described calibration cradle 100A for a three-dimensional scanner according to an embodiment of the present disclosure will be omitted, and components different from those of the above-described calibration cradle 100A will be mainly described.

As illustrated in FIGS. 7 to 10B, the calibration cradle 100B for a three-dimensional scanner according to another embodiment of the present disclosure can be rotated and vertically moved by the movement driver 205.

Here, as illustrated in FIGS. 7 to 10B, the movable case 120 may be provided in contact with the inner peripheral surface of the fixed case 110. However, the outer peripheral surface of the movable case 120 does not necessarily have to be provided in contact with the inner peripheral surface of the fixed case 110, and the inner peripheral surface of the movable case 120 may be provided in contact with the outer peripheral surface of the fixed case 110.

In addition, the movable case 120 is provided to be relatively rotated and vertically moved by the movement driver 205 relative to the fixed case 110 to which the pattern plate 250 is fixed. At this time, it is preferable to place the seat 130 and the pattern plate 250, into which the three-dimensional scanner 1 is inserted and seated, at the center of rotation of the movable case 120 such that the optical axis does not change.

As illustrated in FIGS. 9A and 9B, the movement driver 205 may include a case driving motor 160 having a rotation shaft 161 extending vertically toward the movable case 120, a spur gear 163 provided at the tip of the rotation shaft 161 of the case driving motor 160 to rotate in conjunction with the rotation shaft 161, and a spur internal gear 123 integrally formed on the inner peripheral surface of the movable case 120 and meshing with the spur gear 163.

Here, the case driving motor 160 does not necessarily have to be provided inside the fixed case 110, but may be provided inside a motor case 160C provided to protrude downward from the fixed case 110 and the rotation axis 161 thereof may be disposed to be exposed inside the fixed case 110 as illustrated in FIGS. 9A and 9B.

When the spur gear 163 is rotated following the rotation of the rotating shaft 161 of the case driving motor 160 and meshes with the spur internal gear 123 integrally provided in the movable case 120, the movable case 120 may be relatively rotated relative to the fixed case 110.

In this way, since it is necessary for the spur gear 163 to continuously transmit the rotation force of the case driving motor 160 while meshing with the spur internal gear 123, the meshing should not be released while the movable case 120 moves up and down with respect to the fixed case 110. Therefore, it is preferable to form at least the vertical height of the spur internal gear 123 to correspond to the vertical height of the spiral groove 125 formed on the outer peripheral surface of the movable case 120 to be described later.

Here, the movement driver 205 may include a guide member 175 which penetrates the fixed case 110 so that the tip thereof is inserted into the spiral groove 125 provided on the outer peripheral surface of the movable case 120 to guide the rotational movement of the movable case 120. The spiral groove 125 may be provided to surround the movable case 120 in a spiral shape along the outer peripheral surface of the movable case 120 so as to allow the movable case 120 to simultaneously conduct rotational movement and vertical movement. In addition, the spiral groove 125, which is provided on the outer peripheral surface of the movable case 120, may be grooved in a spiral shape having a predetermined pitch interval so as to allow the movable case 120 to rotate three or more times.

One or more guide members 175 may be provided, and may be, for example, guide bolts. In the case where a plurality of guide members 175 are provided, a pair of guides may be provided to be spaced apart from each other by a predetermined interval (e.g., a 180-degree interval) with reference to the center of the fixed case 110, and the inner ends thereof may be inserted into the spiral groove 125.

Since the tip of the guide member 175 is inserted into the spiral groove 125 provided on the outer peripheral surface of the movable case 120, when the movable case 120 is rotationally moved by the operation of the movement driver 205, the movable case 120 is capable of rotating the three-dimensional scanner 1 while being rotationally moved along the spiral groove 125, and is capable of changing the relative distance between the three-dimensional scanner 1 and the pattern plate 250 in a linear direction while moving upward or downward by the entire pitch distance of the spiral groove 125. At this time, since the pattern plate 250 is disposed to be inclined with respect to the top surface of the installation block 240 fixed inside the fixed case 110, the three-dimensional scanner 1 and the pattern plate 250 may provide various imaging surface angles depending on the rotation of the movable case 120.

Here, the rotating speed and the vertical moving speed of the movable case 120 may be determined by a gear ratio between the spur gear 163 and the spur internal gear 123 on the premise that the case driving motor 160 rotates at the same rotating speed. This is because the spur gear 163 is provided to be directly connected to the rotation shaft 161 of the case driving motor 160.

However, the spur gear 163 does not necessarily have to be directly connected to the rotation shaft 161 of the case driving motor 160. That is, the spur gear 163 may be disposed in parallel to the rotation shaft 161 of the case driving motor 160 and may transmit the driving force of the case driving motor 160 to the spur gear 163 in a belt driving manner.

More specifically, as illustrated in FIGS. 10A and 10B, the movement driver 205 may include a driving pulley 165 provided at the tip of the rotation shaft (not illustrated) of the case driving motor 160, a spur gear 163 disposed in parallel with the rotation shaft of the case driving motor 160, a driven pulley 169 coaxially connected to the rotation shaft of the spur gear 163, and a connection belt 167 rotated by being wound around and meshing with the driving pulley 165 and the driven pulley 169.

At this time, the rotating speed and the vertical moving speed of the movable case 120 may be determined by a combination of primarily the radius ratio between the driving pulley 165 and the driven pulley 169 and secondarily the gear ratio between the spur gear 163 and the spur internal gear 123 on the premise that the case driving motor 160 rotates at the same rotating speed.

Since the movement driver 205 illustrated in FIGS. 10A and 10B is capable of obtaining a more speed reduction ratio by the radius ratio between the driving pulley 165 and the driven pulley 169 compared to the movement driver 205 illustrated in FIGS. 9A and 9B, it may be easier to adjust the speed reduction ratio.

Here, the driving pulley 165, the driven pulley 169, and the connection belt 167 may be provided in the form of gear-meshing with each other. That is, predetermined gear teeth are formed on the outer peripheral surfaces of the driving pulley 165 and the driven pulley 169, and inner peripheral gear teeth capable of meshing with the teeth formed on the outer peripheral surfaces of the driving pulley 165 and the driven pulley 169 may be formed on the inner peripheral surface of the connection belt 167.

On the other hand, compared to the calibration cradle 100A for a three-dimensional scanner according to an embodiment of the present disclosure, the calibration cradle 100B for a three-dimensional scanner according to another embodiment has a configuration in which the movable case 120 moves vertically simultaneously with rotating. Thus, as illustrated in FIGS. 9A and 9B, the vertical movement detector and the pattern rotation detector may be integrally installed as a single sensor unit. At this time, a photo sensor or a Hall sensor may be applied to the sensor unit. The photo sensor unit to which a photo sensor is applied may include a photo sensor 200 fixed to the fixed case 110 under one side of the rotation radius of the movable case 120, and at least one detection lead 200a provided on the rotation radius of the movable case 120 to interact with the photo sensor 200.

Therefore, based on the values of relative distance and rotation angle of the movable distance of the movable case 120 relative to the fixed case 110 measured between the photo sensor 200 and the detection lead 200a, the values of relative distance and rotation angle between the three-dimensional scanner 1 and the pattern plate 250 may be calculated.

Here, the case driving motor 160 may be configured with a stepping motor as described above. In this case, the sensor unit integrally installed to perform the functions of the vertical movement detector and the pattern rotation detector may measure only the relative distance between the three-dimensional scanner 1 and the pattern plate 250 or initial positions of the same, and the rotation angle value may be measured from a preset pulse value of the case driving motor 160 configured with the stepping motor. In addition, when the three-dimensional scanner 1 is stopped after rotating by the operation of the pattern driving motor 210 configured with the stepping motor, the camera 20 of the three-dimensional scanner 1 may operate. Here, the process from rotation to stopping of the three-dimensional scanner 1 may be performed multiple times (e.g., 9 times in total) from the initial position to the completion position of the calibration, and the operation of the camera 20 for conducting the calibration may also be performed the same number of times.

FIG. 11 illustrates a perspective view and a cross-sectional view showing an example of a linear reciprocating movement design of a calibration cradle for a three-dimensional scanner according to an embodiment of the present disclosure.

Although the calibration cradle 100B is illustrated in FIG. 11, the calibration cradle 100A may also be applied.

As described above, in the three-dimensional scanner 1 which is subjected to calibration by using the calibration cradle for a three-dimensional scanner according to an embodiment of the present disclosure, the calibration is conducted after the main body case 10 is at least partially inserted into the movable case 120 in the state in which the tip case 14 is removed. Here, the tip case 14 may be manufactured with various lengths and various specifications, and in this case, it is preferable to set different initial positions of the three-dimensional scanner 1 for conducting calibration.

More specifically, referring to the upper drawing of FIG. 11, the distance between the camera 20 and the optical member 60 in the tip case 14 may be defined as "A," and the distance between the optical member 60 and an object to be measured may be defined as "B." Here, the scan error distance (C) may be set with reference to the distance between the optical member 60 and the object to be measured (B).

Therefore, when conducting calibration using the calibration cradle for a three-dimensional scanner according to an embodiment of the present disclosure, it is preferable to set the distance between the camera 20 and the pattern plate 250 (D) within the range of the sum of half of the scan error distance (C/2) to the distance between the optical member 60 and the object to be measured (B), including the distance between the camera 20 and the optical member 60 (A). In other words, the distance between the camera 20 and the optical member 60 (A) may correspond to the minimum distance for the distance between the camera 20 and the pattern plate 250 (D), and the distance obtained by summing all the distance between the camera 20 and the optical member 60 (A), the distance between the optical member 60 and the object to be measured (B), and half of the scan error distance (C/2) may correspond to the maximum distance for the distance between the camera 20 and the pattern plate 250 (D). Therefore, when conducting calibration, the initial position and the final position of the three-dimensional scanner 1 may be set in consideration of the minimum distance and the maximum distance. In addition, the vertical movement area of the three-dimensional scanner 1 for conducting calibration may be between the initial position and the final position.

As described above, it is necessary to set the initial position of the three-dimensional scanner 1 for conducting calibration differently depending on the distance between the optical member 60 of the tip case 14 provided with various specifications and the camera 20 (A).

For example, assuming that a first tip case 14 in which the length (A) is 95 mm and a second tip case 14 in which the length (A) is 100 mm are manufactured, for both the three-dimensional scanner 1 to which the first tip case 14 is to be applied and the three-dimensional scanner 1 to which the second tip case 14 is to be applied, calibration can be conducted by using the calibration cradle of the present disclosure. At this time, in order to conduct calibration of the three-dimensional scanner 1 to which the first tip case 14 is to be applied, the initial position of the three-dimensional scanner 1 may be set such that the distance between the pattern plate 250 and the camera 20 is closer than that in the case where the second tip case 14 is to be applied.

In contrast, in order to conduct calibration of the three-dimensional scanner 1 to which the second tip case 14 is to be applied, the initial position of the three-dimensional scanner 1 may be set such that the distance between the pattern plate 250 and the camera 20 is farther than that in the case where the first tip case 14 is to be applied.

In the foregoing, embodiments of a calibration cradle for a three-dimensional scanner according to the present disclosure have been described in detail with reference to the accompanying drawings. However, the embodiments of the present disclosure are not necessarily limited by the above-described embodiments, and it will be apparent to a person of ordinary skill in the art that various modifications and equivalents of the present disclosure may be made within the scope of the present disclosure. Therefore, it is to be noted that the true scope of the present disclosure will be determined based on the claims appended hereto.

INDUSTRIAL APPLICABILITY

The present disclosure provides a calibration cradle for a three-dimensional scanner in which a pattern plate is configured to automatically move when the three-dimensional scanner is inserted and seated in order to conduct more accurate calibration of the three-dimensional scanner and to improve user convenience.

What is claimed is:

1. A calibration cradle for a three-dimensional scanner, the calibration cradle comprising:

a fixed case having an internal space formed therein;

a pattern plate provided inside the fixed case and provided to calibrate the three-dimensional scanner comprising a camera;

a movable case into which at least a portion of the three-dimensional scanner is inserted such that the camera faces the pattern plate, the movable case being configured to move to allow the three-dimensional scanner to move by at least one of rotational movement or vertical movement; and a movement driver configured to provide a driving force to move at least one of the movable case or the pattern plate, wherein the movement driver comprises:

a case mover configured to vertically move the movable case; and a pattern mover configured to rotationally move the pattern plate, and wherein when the case mover and the pattern mover stop, the camera operates to conduct calibration, and at least one of the case mover or the pattern mover moves.

2. The calibration cradle of claim 1, wherein the movable case is vertically moved by the movement driver, wherein the pattern plate is disposed inside the fixed case to be inclined to one side and is rotationally moved by the movement driver, and wherein while the movable case or the pattern plate moves, an angle between an optical axis of light emitted from the three-dimensional scanner to the pattern plate and a rotation axis of the pattern plate is maintained.

3. The calibration cradle of claim 1, wherein the case mover comprises:

a case driving motor penetrating a movable panel provided in a horizontal direction to be connected to the movable case inside the movable case; and at least one panel guide configured to guide the vertical movement of the movable panel.

4. The calibration cradle of claim 1, wherein at least one of a vertical movement detector configured to detect the vertical movement of the movable case or a pattern rotation detector configured to detect a rotation of the pattern plate is provided inside the fixed case.

5. The calibration cradle of claim 1, wherein a seat in which at least a portion of the three-dimensional scanner is seated is provided on a top surface of the movable case, and wherein a mounting sensor configured to detect seating of the three-dimensional scanner is provided in the movable case adjacent to the seat.

6. The calibration cradle of claim 5, wherein the mounting sensor is provided in a form of a tact switch that comes into contact with the three-dimensional scanner inserted through the seat.

7. The calibration cradle of claim 1, wherein the movable case is rotationally moved and vertically moved by the movement driver, and wherein the pattern plate is fixed inside the fixed case to be inclined to one side.

8. The calibration cradle of claim 7, wherein while the movable case rotationally moves and vertically moves, an angle between an optical axis of light emitted from the three-dimensional scanner to the pattern plate and the pattern plate is maintained.

9. The calibration cradle of claim 1, wherein the movable case is provided inside the fixed case to be in contact with an inner peripheral surface of the fixed case, wherein the movement driver comprises:

a case driving motor having a rotation shaft extending vertically toward the movable case; and a guide member extending through the fixed case such that a tip is inserted into a spiral groove formed on an outer peripheral surface of the movable case to guide the rotational movement of the movable case, and wherein the spiral groove is provided to surround the movable case in a spiral form along an outer peripheral surface of the movable case so that the movable case can simultaneously conduct the rotational movement and the vertical movement.

10. The calibration cradle of claim 9, wherein the movement driver comprises:

a spur gear connected to and rotated in conjunction with the rotation shaft of the case driving motor; and a spur internal gear formed on an inner peripheral surface of the movable case and meshing with the spur gear.

11. The calibration cradle of claim 10, wherein the spur internal gear is formed on an inner peripheral surface of the movable case and has a vertical height corresponding to a vertical height of the spiral groove.

12. The calibration cradle of claim 9, wherein the movement driver comprises:

a driving pulley provided at a tip of the rotation shaft of the case driving motor;

a spur gear disposed in parallel with the rotation shaft of the case driving motor;

a driven pulley coaxially connected to the rotation shaft of the spur gear; and a connection belt configured to rotate by being wound around and meshing with the driving pulley and the driven pulley, wherein the driving pulley, the driven pulley, and the connection belt are provided in a form of gear-meshing with each other.

13. The calibration cradle of claim 1, wherein the movement driver is operated by receiving power from a rechargeable battery provided in the fixed case, and wherein the rechargeable battery is configured to be charged in a wireless or wired manner.

14. The calibration cradle of claim 1, wherein the three-dimensional scanner includes a light projector configured to emit light, and wherein the light emitted from the light projector is directly emitted onto the pattern plate without refraction.

15. The calibration cradle of claim 14, wherein when the three-dimensional scanner is inserted into the movable case in a state in which a tip case comprising an optical member configured to refract the light is removed, an initial position for the three-dimensional scanner to conduct calibration is set to vary depending on a distance between the camera and the optical member of the removed tip case.

* * * * *